United States Patent
Wolcott et al.

[19]

[11] Patent Number: 6,079,313
[45] Date of Patent: Jun. 27, 2000

[54] PULSELESS, REVERSIBLE PRECISION PISTON-ARRAY PUMP

[75] Inventors: Duane K. Wolcott, Baton Rouge, La.; Graham D. Marshall, Fox Island, Wash.

[73] Assignee: FIA Solutions, Inc., Gig Harbor, Wash.

[21] Appl. No.: 09/292,971

[22] Filed: Apr. 16, 1999

Related U.S. Application Data

[62] Division of application No. 08/704,814, Aug. 28, 1996.

[51] Int. Cl.[7] .................................................. F01B 3/04
[52] U.S. Cl. ................................ 92/71; 417/269; 91/499
[58] Field of Search ................................ 417/269; 92/71; 91/499

[56] References Cited

U.S. PATENT DOCUMENTS

| | | | |
|---|---|---|---|
| 2,310,459 | 2/1943 | Potter | 210/40 |
| 2,518,619 | 8/1950 | Huba | 103/173 |
| 2,745,350 | 5/1956 | Capsek | 103/41 |
| 3,981,360 | 9/1976 | Leduc et al. | 417/269 |
| 4,095,921 | 6/1978 | Hinaga et al. | 417/269 |
| 4,360,321 | 11/1982 | Copp, Jr. et al. | 417/269 |
| 4,880,361 | 11/1989 | Ikeda et al. | 417/269 |
| 5,009,574 | 4/1991 | Ikeda et al. | 417/222 |
| 5,167,181 | 12/1992 | Ken Lee | 91/499 |
| 5,253,981 | 10/1993 | Yang et al. | 417/3 |
| 5,733,105 | 3/1998 | Beckett et al. | 417/269 X |

*Primary Examiner*—Timothy S. Thorpe
*Assistant Examiner*—Ehud Gartenberg
*Attorney, Agent, or Firm*—Reginald F. Roberts, Jr.

[57] ABSTRACT

A pulseless, reversible, precision piston-array pump. The pump head has a cylindrical body which rotates inside a cylindrical casing. A cam cap closes one end of the pump body, and a port cap the other end. The cam cap has on its interior surface a groove which controls the timing and depth of the piston strokes. The port cap has on its interior surface an inlet valve groove and an outlet valve groove to provide the valving action which controls the direction of fluid flow. At all times during the operation of the pump, at least one piston is in a compression mode; At least one piston is in a suction mode; and at least one piston is in a null mode, performing neither compression nor suction while moving across the port cap. This design decouples the rotary movement of the cylindrical body from the linear movement of the pistons, to provide pulseless flow for the pump.

10 Claims, 13 Drawing Sheets

ROTOR DETAIL

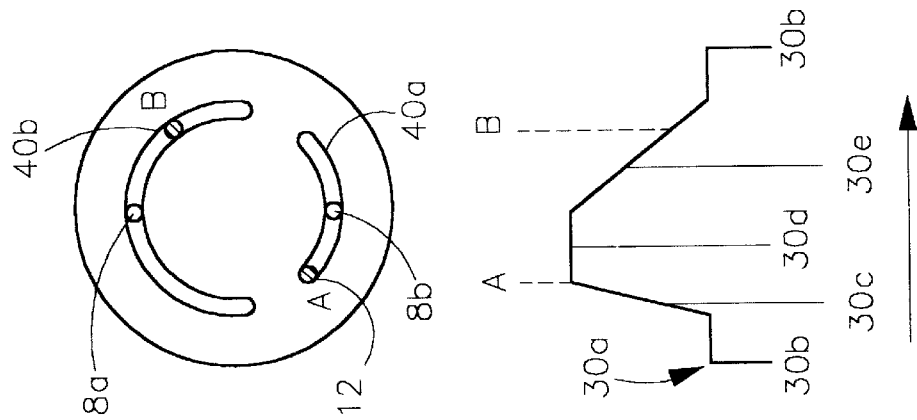
FIGURE 5C
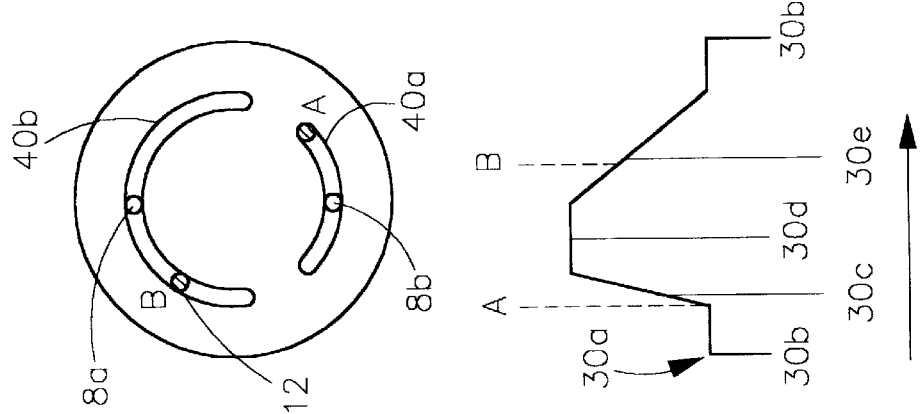
FIGURE 5B
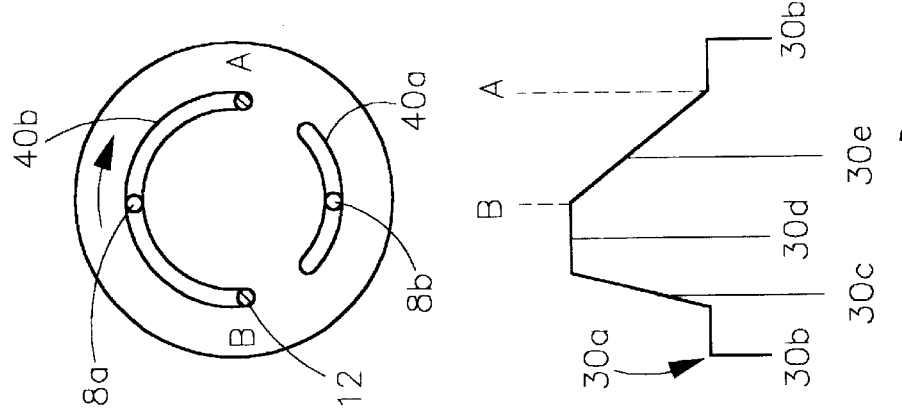
FIGURE 5A
FIGURE 5

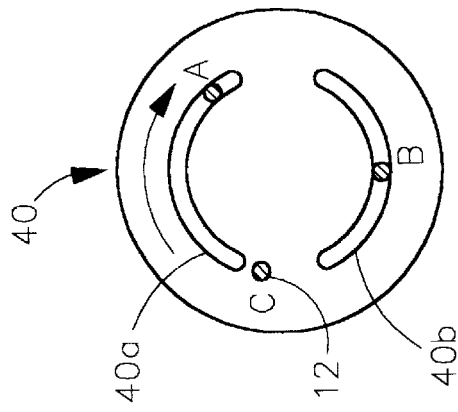 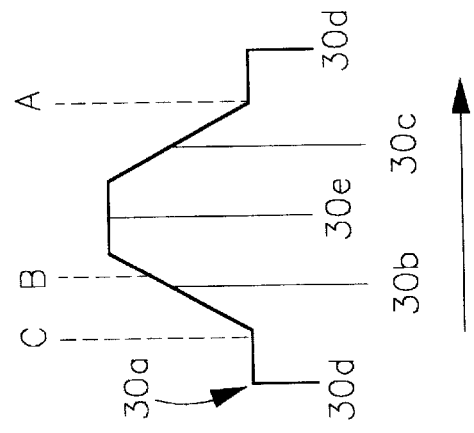
FIGURE 6A
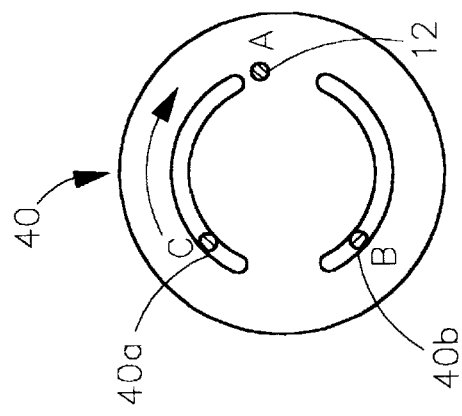 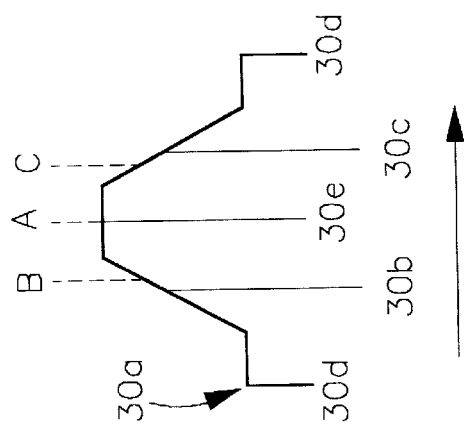
FIGURE 6B
FIGURE 6
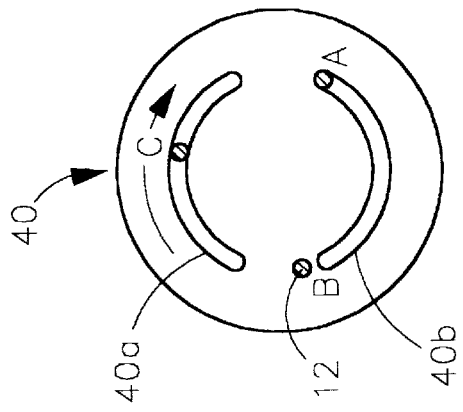 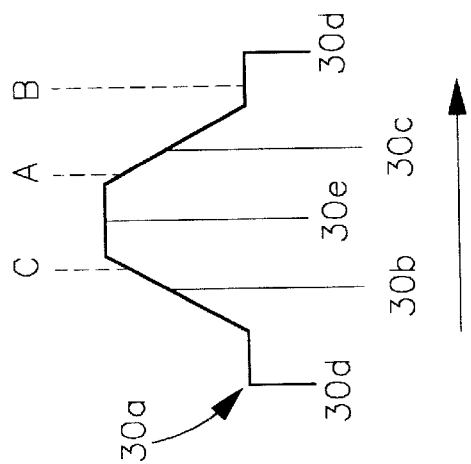
FIGURE 6C

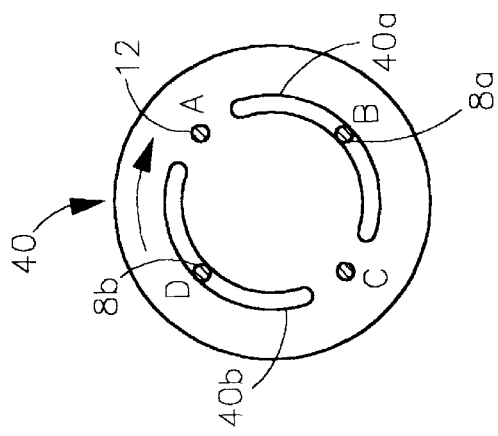
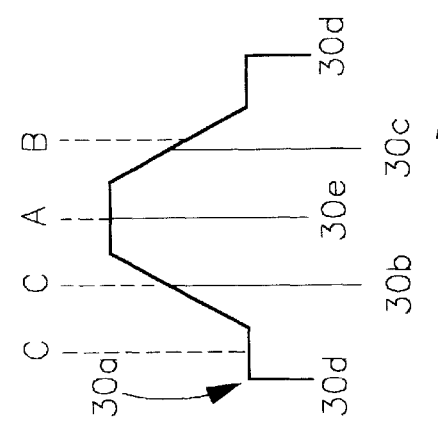
FIGURE 7A
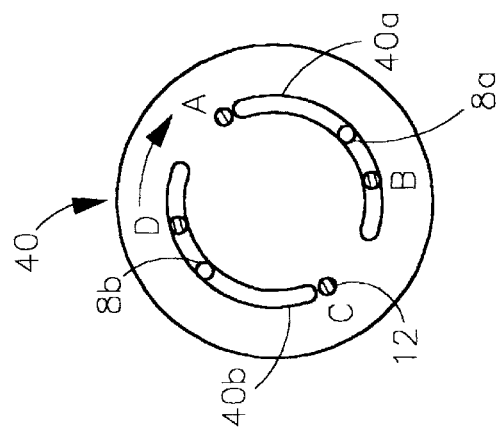
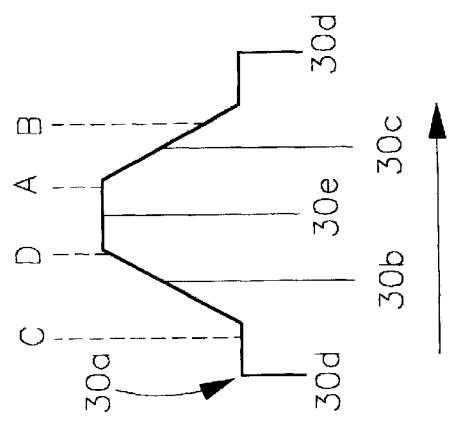
FIGURE 7B
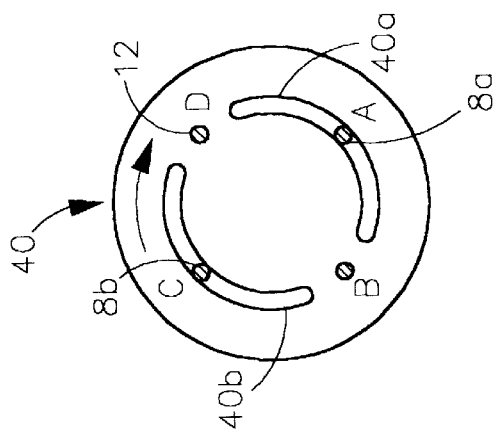
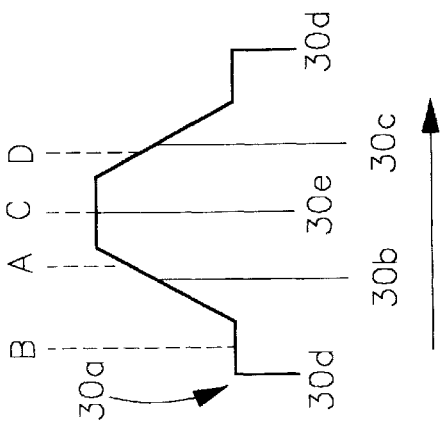
FIGURE 7C
FIGURE 7

Piston Layout Detail

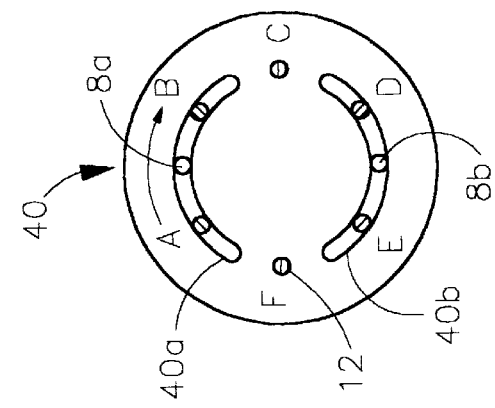
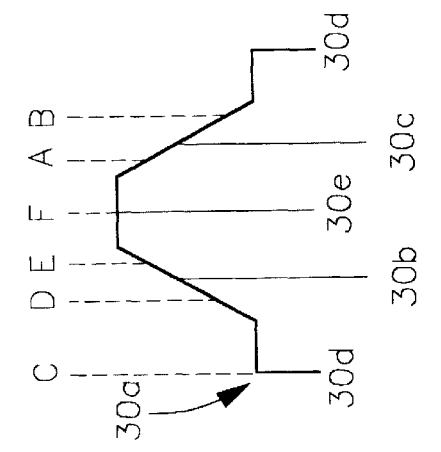
FIGURE 9A
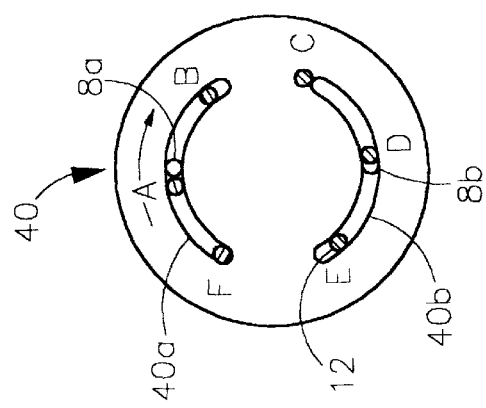
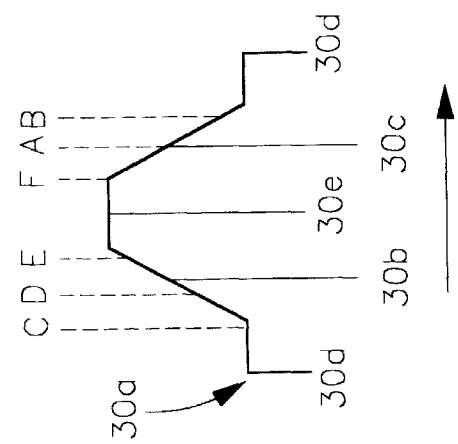
FIGURE 9B
FIGURE 9
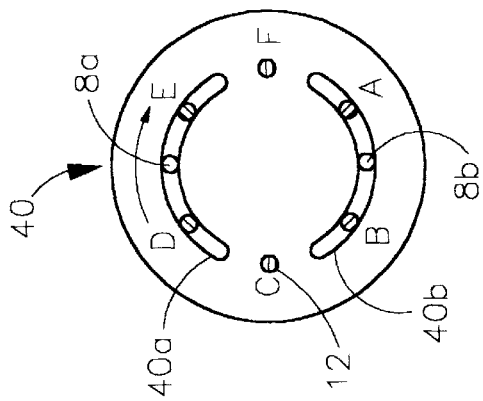
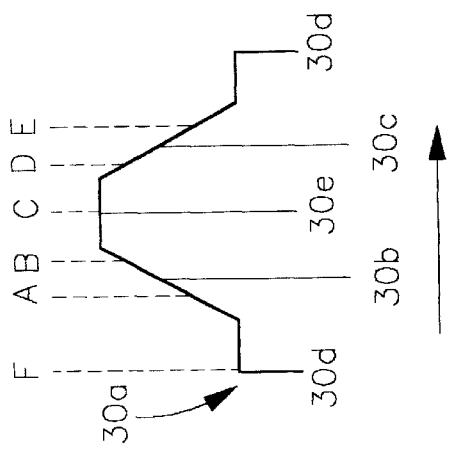
FIGURE 9C

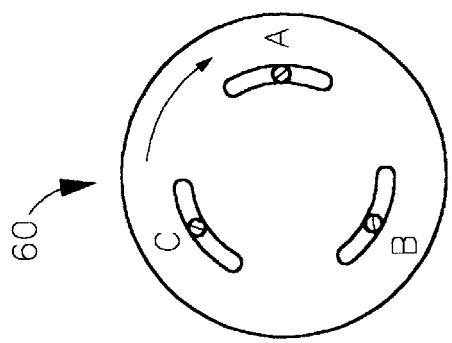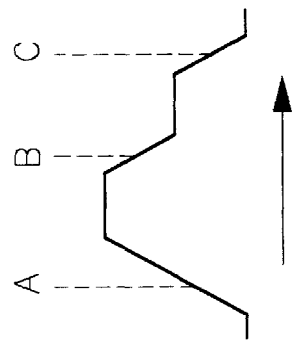
FIGURE 14D
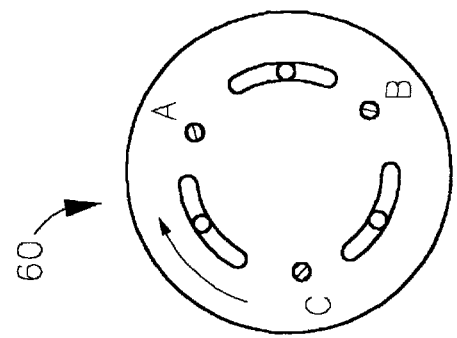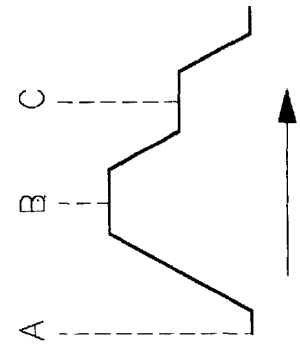
FIGURE 14C
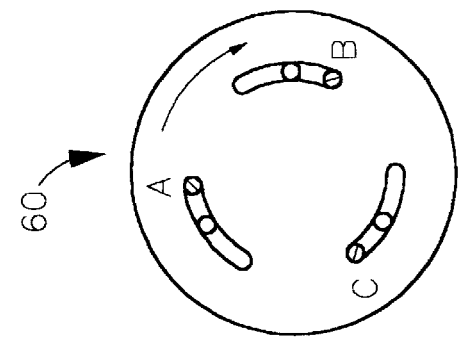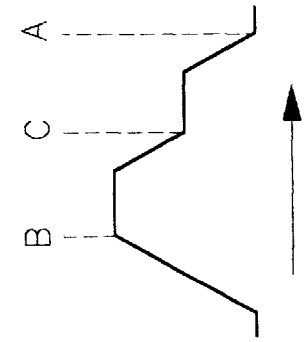
FIGURE 14B
FIGURE 14

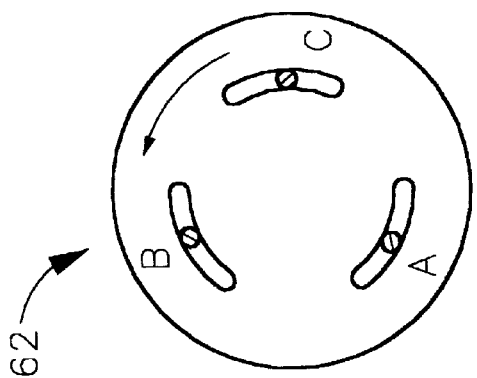
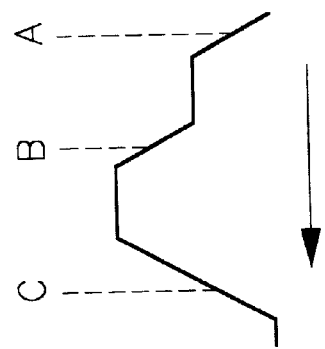
FIGURE 15D
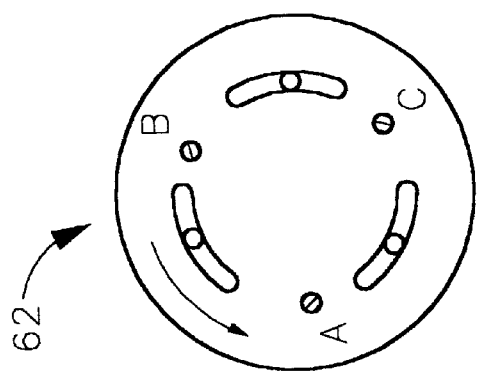
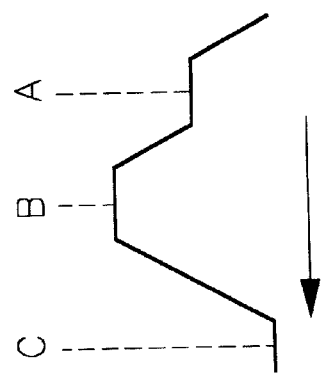
FIGURE 15C
FIGURE 15
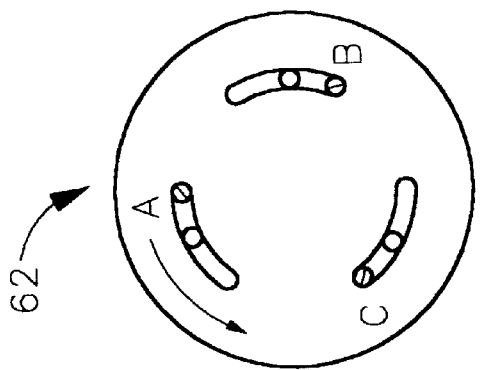
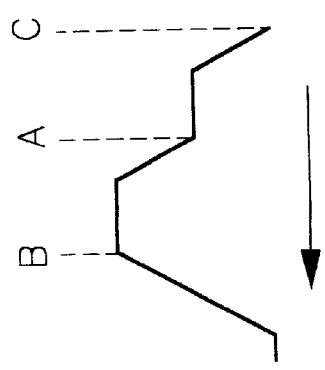
FIGURE 15B

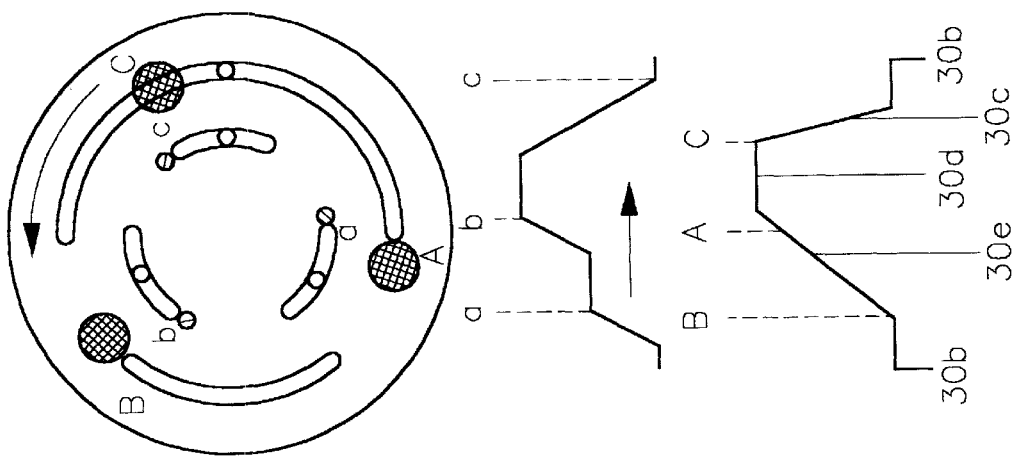
FIGURE 16D
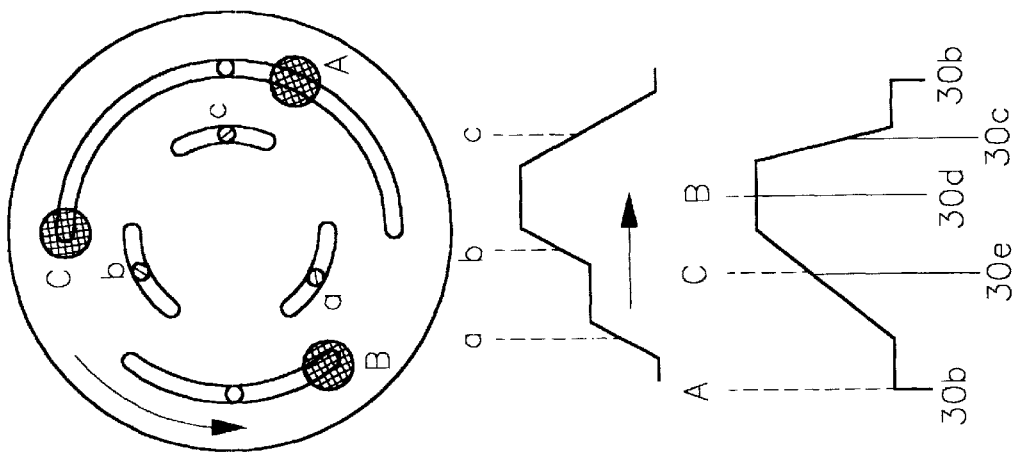
FIGURE 16C
FIGURE 16
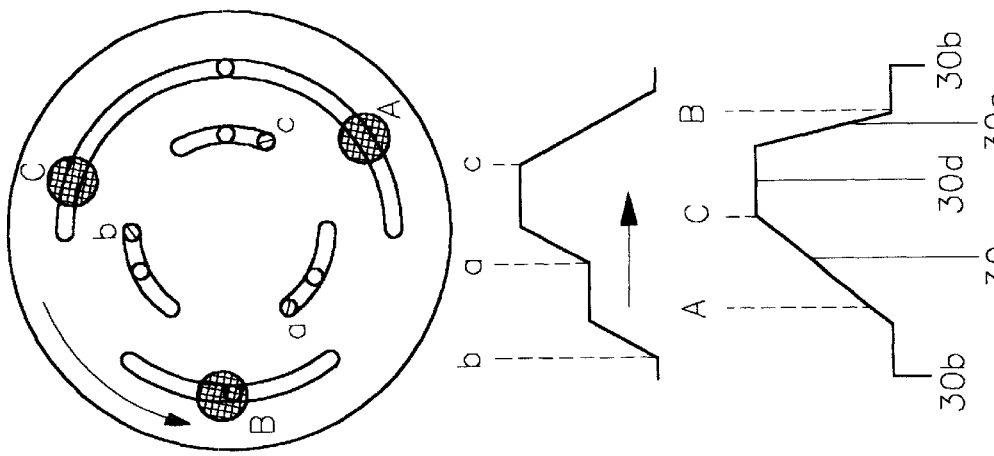
FIGURE 16B

PULSELESS, REVERSIBLE PRECISION PISTON-ARRAY PUMP

This is a division of application Ser. No. 08/704,814, filed Aug. 28, 1996.

BACKGROUND OF THE INVENTION

The present invention relates to mechanical pumps. More particularly, the invention relates to piston-array pumps suitable for use in analytical instrumentation.

There are many different categories of pumps commonly used in instrumentation. Examples include such types as: centrifugal, diaphragm, gear, peristaltic, piston, and syringe. This evaluation will cover the mode of operation and advantages and disadvantages of each. In particular, the relevance of the characteristics of each type to FIA (Flow-Injection Analysis), SIA (Sequential Injection Analysis), and HPLC (High Pressure Liquid Chromatography) will be examined. These methodologies will hereafter be referred to as "Flow-Based Analytical Techniques".

Centrifugal pumps are typically not used directly in the analytical portions of instrumentation, as they are incapable of delivering sufficiently precise control of flow. They do, however, find use as sample loop circulation devices. They have the disadvantages of not being self-priming, are uni-directional in their pumping action, and cannot pump against much back pressure. They have the advantages of not requiring the use of check valves to regulate cycle direction, and of providing pulseless flow output. Use of this type of pump to provide micro-flows is highly unlikely, and they are typically not used in Flow-Based Analytical Techniques.

Diaphragm pumps have several advantages over centrifugal. They are self-priming, and they will pump against more back pressure. Again, precise flow control is not possible, pumping action is unidirectional, they require check valves to control gird flow direction, and they deliver highly pulsating flows. These pumps, like centrifugal pumps, are usually used only to drive sample loop flows. Use of this type of pump to provide microflows is unlikely, and this type, too, is not usable in Flow-Based Analytical Techniques.

Gear pumps have advantages over both centrifugal and diaphragm pumps. Like diaphragm pumps, they are self-priming, can pump against more back pressure than centrifugal pumps, and can provide higher output pressures than centrifugal pumps. Like centrifugal pumps, their output is pulseless. Unlike centrifugal or diaphragm units, gear pumps can pump either backwards or forwards, and require no check valves. Precise control of flow rate is difficult, as the gearing surfaces are difficult to seal against "slip leakage", and precise flow control becomes problematical when pumping against high back pressure. Gear pumps are also more vulnerable to damage from particulate matter, which causes mechanical wear and increases the "slip leakage" problem. One gear pump version (an experimental design produced by Transcience) purports to eliminate slip leakage by using elastomeric gears. The limiting problem with the Transcience pump is likely to be longevity—the elastomeric gearing will probably not deliver long time intervals without failure, due to rapid wear of the gears. This type of pump (Transcience) purports to deliver micro-flow capability. The Transcience pump is intended for use in the FIA/SIA market niche. It will not be usable in HPLC due to low pressure limitations.

Peristaltic pumps are self-priming, can pump against more back pressure than centrifugal pumps, require no check valves to regulate flow direction, and can pump bidirectionally. They have the significant advantage of being able to gang multiple pumping heads on a single drive unit, and delivering all flows "in phase". The flows delivered by peristaltic pumps are "pulsating"—to a lesser extent than piston pumps, but still significantly. The really significant problem with peristaltic devices is the rapid failure of the elastomeric pump tubing used due to "plastic fatigue" from mechanical wear. Micro-flow delivery from this pump type is problematic due to the very small i.d. pump tubing required. This is the current pump of choice for laboratory FIA, it can also be used for SIA, but not for HPLC due to low pressure limits. Use of peristaltic pumps in instrumentation for process control is unacceptable due to the high maintenance requirements caused by pump tube wear.

Piston pumps are self-priming, can pump against the most back pressure of any pump type available, and can deliver very precise and easily regulated flow velocities. They provide significantly pulsing flow, pump unidirectionally, and most types require the incorporation of check valves. This type of pump can easily be designed to deliver micro-flow capability, and can be configured to drive multiple heads with a single drive unit. This type of pump is suitable for FIA, provided the detector can tolerate some flow pulsation. It cannot be used in SIA due to its unidirectional pumping action. It is the pump of choice for most HPLC work, and in instrumentation for process control, due to its high reliability. ELDEX is a manufacturer of a unit typical of this type of pump. Piston pumps for instrumentation are usually designed primarily for HPLC, which requires pressure capabilities significantly higher than FIA or SIA (1000–5000 psi), and thus makes them relatively expensive, which expense increases rapidly if multiple streams must be pumped.

A unique subset of piston pumps is produced by FMI, Inc. This pump utilizes a special pumping cycle incorporating a piston that simultaneously reciprocates (providing pumping action), and rotates (providing valving action). This type of pump is self-priming, can pump against significant back pressure (but less than pumps designed specifically for HPLC), has no check valves, can deliver bi-directional pumping action, and allows very precise and easily regulated flow velocities. The pumping action is inherently pulsating. These pumps can easily deliver micro-flow capability, and can be configured to drive multiple heads with a single drive unit. They are suitable for FIA, and as they are bi-directional, can be used in SIA (again, with the limitation that the detector tolerate flow pulsation). They are not suitable for HPLC due to low output delivery pressure.

Syringe pumps are essentially very large piston pumps. They are self-priming, can deliver very high pressures, and, as long as their initial fill charge lasts, can deliver pulseless flow rates. They can easily be designed to deliver microflows. However, their cycle does require a long refill cycle once the fill charge is exhausted, which is a potential problem (and one soluble by using duplex syringe pumps). They also require some sort of external valving arrangement to control the fill/pump cycle. This type of pump (especially if used in a duplex configuration) is suitable for FIA, SIA, and HPLC. Practical experience has shown glass-barreled syringe pumps to be fragile, and a need to exercise care with the syringe barrel and plunger.

Prior art relating specifically to piston-array pumps include the following patents.

U.S. Pat. No. 2,518,619 to Huber discloses a cylindrical ring valve for multicylinder pumps.

U.S. Pat. No. 3,981,630 to Leduc et al. discloses a swash-plate pump wherein a plurality of pistons bear against the swash plate and are given a reciprocating movement when the plate is rotated by a drive shaft.

U.S. Pat. No. 4,880,361 to Ikeda et al. discloses a multi-piston swash-plate compressor for an air-conditioning system used in a motor vehicle. The compressor has combined cylindrical blocks closed at both axial end faces thereof by front and rear housings.

U.S. Pat. No. 5,009,574 to Ikeda et al. discloses a swash-plate compressor having a pair of axially combined front and rear cylindrical blocks forming therein a plurality of cylindrical bores, a swash-plate chamber, and an oil chamber in which lubricating oil is stored to be stirred by a swash plate rotatably received in the swash-plate chamber, a drive shaft centrally and rotatably mounted in the combined cylindrical blocks to effect rotation of the swash plate, a plurality of reciprocatory double-headed pistons slidably fitted in the bores and operatively engaged with the swash plate via shoe members to be reciprocated by the rotation of the swash plate, a pair of thrust bearings axially supporting the swash plate, and front and rear housings having suction chambers for the refrigerant gas after compression. The front housing has a shaft-sealing chamber formed therein and separated from the suction chamber thereof to define an intermediate pressure chamber between the high-pressure swash-plate chamber and the low-pressure suction chamber of the front housing, and a thin fluid passageway interconnecting the shaft-sealing chamber with the suction chamber. The intermediate pressure chamber and the lad thin fluid passageway prevent evacuation of the lubricating oil from the swash-plate chamber to the suction chamber even during the rotation of the compressor at a high speed, to thereby promote a lubrication of the thrust bearings, the shoes, and the swash plate.

U.S. Pat. No. 4,095,921 to Hiraga et al. discloses a multi-cylinder compressor suitable for use in a vehicular air-conditioning system. The compressor includes a pair of axially-spaced cylindrical blocks for receiving a refrigerant fluid therein for compression. First and second sets of pistons are respectively reciprocated within the front and rear cylinders, respectively, by first and second sets of rods of different axial lengths. A lubricating system for the compressor includes a flapper element located near the oil hole, to direct oil to the shaft seal for both clockwise and counterclockwise rotation of the compressor.

U.S. Pat. No. 2,475,350 to Capsek discloses a fuel-injection pump comprising a series of elementary parallel piston pumps arranged circularly about the longitudinal axis of the assembly.

U.S. Pat. No. 4,360,321 to Copp, Jr. et al. discloses a multi-cylinder refrigerant compressor having double-ended pistons operating in aligned cylinder bores of a cylinder block to discharge refrigerant from the opposite ends thereof to discharge chambers formed in opposite ends of the compressor. A muffler arrangement is completely formed within the compressor, and comprises a separate attenuation chamber ported at one of two opposing ends thereof directly to each discharge chamber. Each attenuation chamber is formed within and as an integral part of the cylinder block between two adjacent cylinder walls thereof, and an elongated attenuation passage directly connects the attenuation chambers at their other ends. The attenuation chamber is also formed in and as an integral part of the cylinder block, and extends between the two adjacent cylinder walls. The volumes of the attenuation chambers are substantially equal, and the length of the attenuation passage is substantially longer than the corresponding longitudinal dimension of the attenuation chambers in order to attenuate the refrigerant discharge pulses admitted to the discharge chambers to an acceptable output level totally within the compressor.

None of these prior-art pumps is capable of providing the precise, pulseless, and reversible flow of fluid action necessary for chemical analysis. A need therefore exists for a pump which provides such capability. Such a pump, which would have great versatility, is provided by the present invention.

SUMMARY OF THE INVENTION

In general, the present invention in a first aspect provides a pump head for a piston-array pump. The pump head comprises (a) a cylindrical casing having first and second ends; (b) a cylindrical body having first and second ends, rotatably disposed within the casing; (c) a cam cap at the first end of the cylindrical body; (d) a port cap at the second end of the cylindrical body; (e) an inlet port; (f) an outlet port; (g) a plurality of pistons; (h) a cam follower for each piston; and (i) reciprocating means. The cam cap, cam followers, and pistons are constructed and arranged so that at all times during which the pump head is rotating at least one piston is in a compression mode; at least one piston is in a suction mode; and at least one piston is in a null mode, performing neither compression nor suction while traversing the surface of the port cap, thereby decoupling the rotational movement of the cylindrical body from the linear movement of the pistons to provide pulseless flow by the pump.

In a second aspect the invention provides a cam cap for a pump head of a piston-array pump. The pump head has a cylindrical casing, a cylindrical body rotatably disposed within the casing, a plurality of pistons disposed within the cylindrical body, and a cam follower for each piston. The cam cap comprises (a) a circular disk, and (b) a groove on the interior surface of the disk. The groove defines a geometric figure which (c) is circular; (d) has a substantially semicircular cross-section; (e) has a lowest surface, a highest surface, and a plurality of sloping surfaces connecting the lowest and highest surfaces to one another; and (f) in combination with the cam followers controls the timing and depth of the strokes of the pistons. The cam cap, cam followers, and pistons are constructed and arranged so that at all times during which the cylindrical body is rotating at least one piston is in a compression mode; at least one piston is in a suction mode; and at least one piston is in a null mode, performing neither compression nor suction, thereby decoupling the rotational movement of the cylindrical body from the linear movement of the pistons to provide pulseless flow by the operation of the pump.

In a third aspect, the invention provides a method for merging and/or ratio-blending aliquants from two different streams in a first channel, and for utilizing a second channel to propel the merged and blended aliquants through a separate, pumped carrier channel. The method comprises the provision of a pump head having a plurality of pistons, a plurality of inlet ports, and a plurality of outlet ports. The pumphead is further provided with a port cap having a plurality of valve grooves which control the direction of fluid flow. At least one of the valve grooves is utilized to control the direction of flow of a fluid sample, and at least one to control the direction of flow of a fluid reagent. The sample and reagent fluids are expelled in a manner which joins and blends them in a single flow path. The carrier fluid is then ejected immediately thereafter into the now-common flow path of the sample and reagent fluids, thereby propelling the merged sample and reagent fluids to whatever receptor is desired.

BRIEF DESCRIPTION OF THE DRAWINGS

FIG. 5A, 5B, and 5C are schematic representations of a port cap for the type of pump shown in FIG. 1, which utilizes two pistons, showing the positions of the pistons.

FIG. 6A, 6B, and 6C are schematic representations of a port cap of the type pump shown in FIG. 1 which uses three pistons, showing the positions of the pistons, and representing the piston motion during three phases of a pump cycle.

FIG. 7A, 7B, and 7C are schematic representations of a port cap for a pump of the type shown in FIG. 1 using four pistons, and representing the piston positions in three phases of a pump cycle.

FIG. 9A, 9B, and 9C are schematic representations of a port cap for a pump of the type shown in FIG. 1 which uses six pistons, and representing the piston position in three phases of a pump cycle.

FIG. 14A, 14B, 14C, and 14D are schematic representations of a second embodiment of a port cap for a pump made in accordance with the principles of the present invention.

FIG. 15A, 15B, 15C, and 15D are schematic representations of a third embodiment of a port cap for a pump made in accordance with the principles of the present invention.

FIG. 16A, 16B, 16C, and 16D are schematic representations of a fourth embodiment of a port cap for a pump made in accordance with the principles of the present invention.

DETAILED DESCRIPTION OF THE INVENTION

Figure 1:
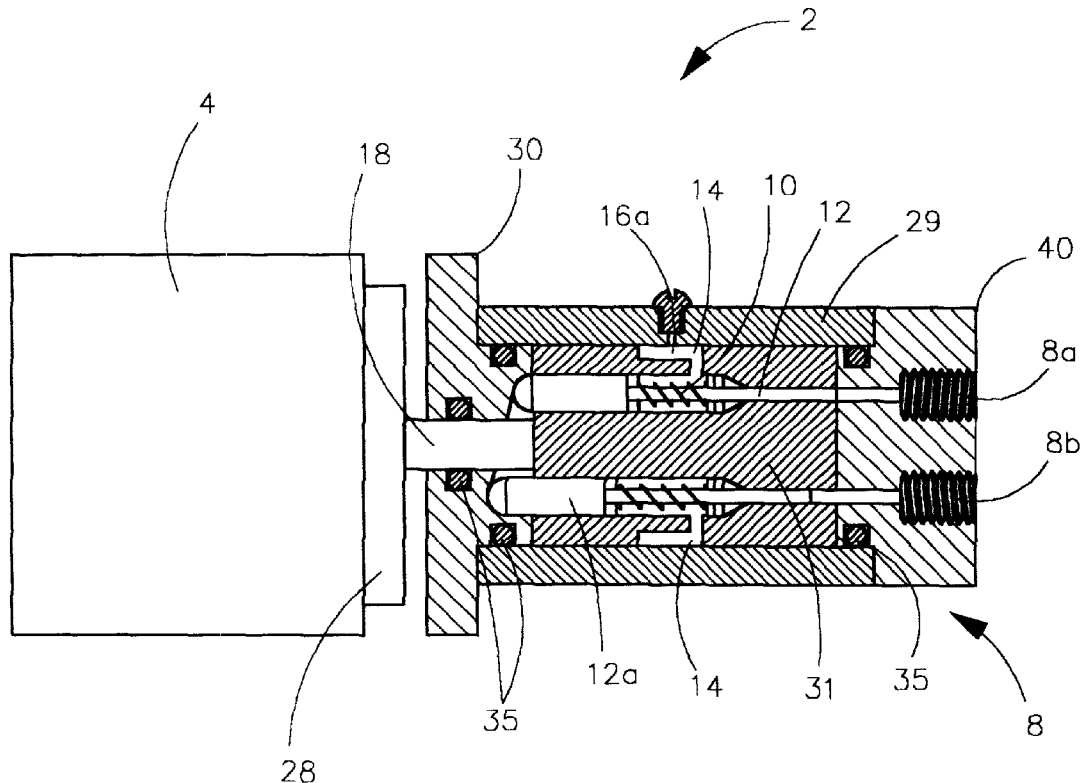
FIG. 1 is a vertical longitudinal cross-section, partly schematic, of an embodiment of a pump made in accordance with the principles of the present invention.
Figure 2:
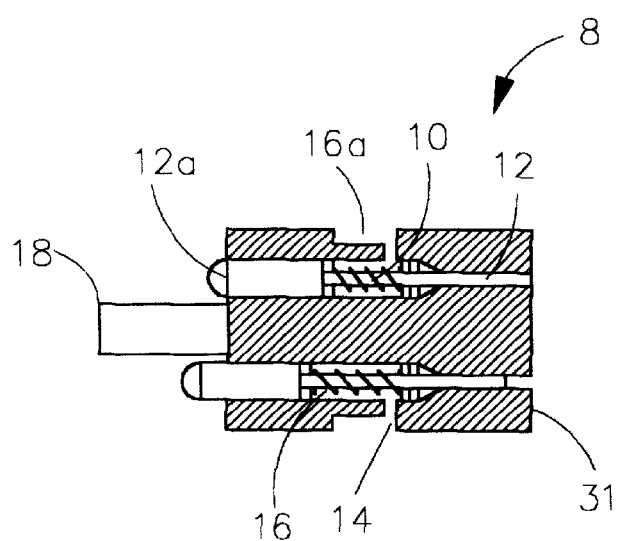
FIG. 2 is a schematic representation of the rotor element of the head of the pump shown in FIG. 1.

More specifically, reference is made to FIG. 1, in which is shown a pump made in accordance with the principles of the present invention, generally designated by the numeral 2, and to FIG. 2, in which is shown the internal structure of a portion of the pump 2.

The pump 2 comprises a motor 4 and a drive train represented schematically and designated by the numeral 28, joined by a drive shaft 18. The pump 2 further comprises a pump head 8 having a cylindrical casing 29, a cylindrical body 31 rotatably disposed within the casing 29, a cam cap 30, a port cap 40 (shown in FIG. 4), an inlet port 8a, and an outlet port 8b. Within the cylindrical body 31 are disposed a plurality of pistons 12 having cam followers 12a and compression springs 10 disposed in cylinders 16, lubricant cycle ports 14, and lubricant reservoir 16a. The cylindrical body 31 rotates inside the cylindrical housing, with the cam cap 30 at one end and the port cap 40 at the other end of the body 31.

The motor 4 which drives the pump head 8 is preferably a micro-stepper electrical motor, which provides maximum cycle flexibility. The motor 4 is coupled to the pump head 8 by anti-backlash bevel gears (not shown), which are perpendicular to one another. This gearing configuration has several advantages. Mounting the motor 4 perpendicular to the head 8 results in a space-conserving design which requires a minimal depth behind a mounting panel (not shown). The use of the anti-backlash gears eliminates potential errors which might be caused by gearing wear. Moreover, the gearing arrangement provides at least a three-to-one mechanical advantage, thereby allowing the pump head 8 to be driven by a lower-power motor 4 than would be required if a direct drive were used.

The mounting bracket—head configuration permits the pump head 8 to be separated from the drive motor 4 by a barrier (not shown). Using seals (not shown) at this locus should allow the pump 2 to be used in explosion-proof safety areas. Multiple redundant seals within the pump head 8 would make it very unlikely that sample fluid (not shown) would come into contact with a source of ignition. However, even if such seals are not included, the angular mounting of the motor 4 above and behind the pump head 8 eliminates the possibility that any sample or reagent fluid (not shown) might leak in such a manner as to cause an electrical problem.

Figures 3, 3A, 3B:
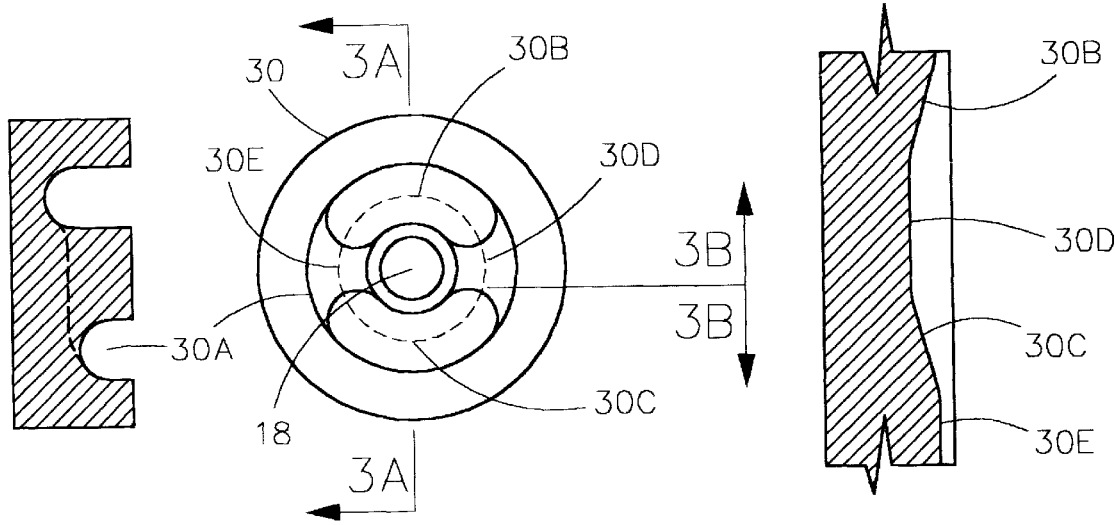
FIG. 3 is a plan view of a cam cap for the pump shown in FIG. 1.
FIG. 3A is a cross-section of the cam cap shown in FIG. 3, taken along the cutting line 3A—3A.
FIG. 3B is a cross-section of the cam cap shown in FIG. 3, taken along the cutting line 3B—3B.

Reference is now made to FIG. 3, in which is shown the structure of the cam cap 30 wherein the drive shaft 18 is disposed. A cam groove 30a on the interior surface of the cap 30 provides a surface having differences in elevation at 30b, 30c, 30d, and 30e, as indicated in FIG. 3B, to which reference is now made. The cam cap 30 comprises a circular disk having interior and exterior surfaces. The interior surface of the cam cap 30 includes a groove 30a having a lowest surface 30d, a raised surface 30e, and sloping surfaces 30b and 30c. Referring now to FIG. 3A, cam groove 30a defines a geometric figure which is circular and which has a substantially semicircular cross-section: however, a retangular or triangular cross section may also be used. The groove 30a functions as a cam to control the timing and depth of the piston 12 stroke.

Figure 4:
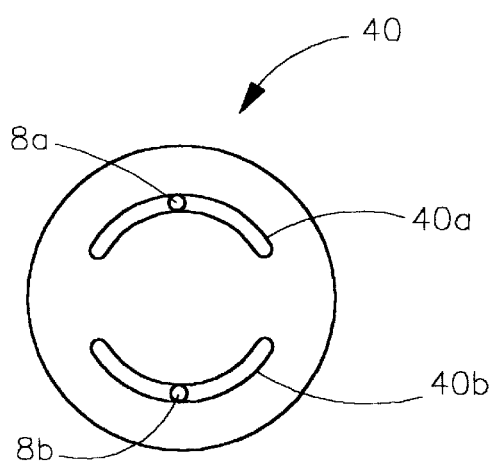
FIG. 4 is a plan view of a port cap for the pump shown in FIG. 1.
Figure 15A:
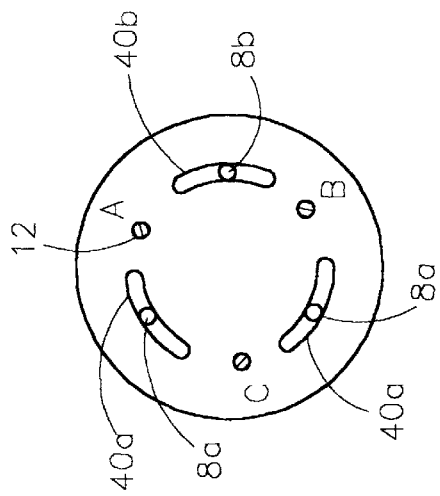
Figure 14A:
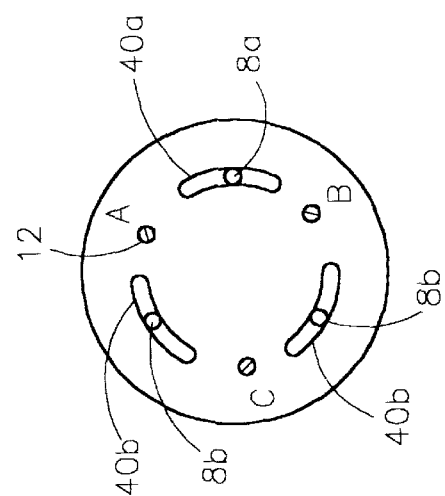

Reference is now made to FIG. 4, in which is shown the structure of the port cap 40, which comprises a circular disk having inlet and outlet ports 8a and 8b, respectively, and on its interior surface valve grooves 40a and 40b. The ports 8a, 8b and grooves 40a, 40b provide the valving action to control the direction of fluid flow. Since the valving-control device is not part of the piston 12 (see FIGS. 1 and 2), the pistons 12 can be made much smaller in diameter than in prior-art piston pumps. The precisely-controlled inter-operation of the rotating body 31 of the pump head 8, valve grooves 40a, 40b, and cam groove 30a allow the pump 2 to deliver precise and nonpulsating flow in either direction without the use of check valves.

A unique feature of the present invention is the introduction of the null motion, which decouples the rotational position from the piston-traverse position, and thereby provides essentially pulseless flow. In prior-art dual-piston ninety-degree offset pump systems, there is always some flow disturbance at the "cross-over point." The null-traverse feature eliminates and solves this problem, since at least one piston 12 is loading, and at least one piston 12 dispensing during any given period of time, while other pistons 12 are traversing the null position. The pumping action is analogous to that of a peristaltic or gear pump, but by retaining the pistons 12 and seals (not shown) provides more efficient sealing and higher outlet pressures, as well as greater longevity due to non-use of elastomeric mechanical components. The pump 2 should give the best long-term performance, as well as delivering pulseless and reversible microflow.

Figure 10A:
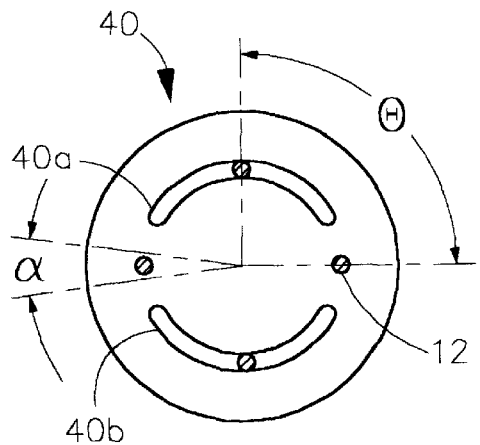
FIG. 10A and 10B are schematic representations of a generic port cap of the pump shown in FIG. 1, showing certain angular parameters which are critical to the present invention.
Figure 10B:
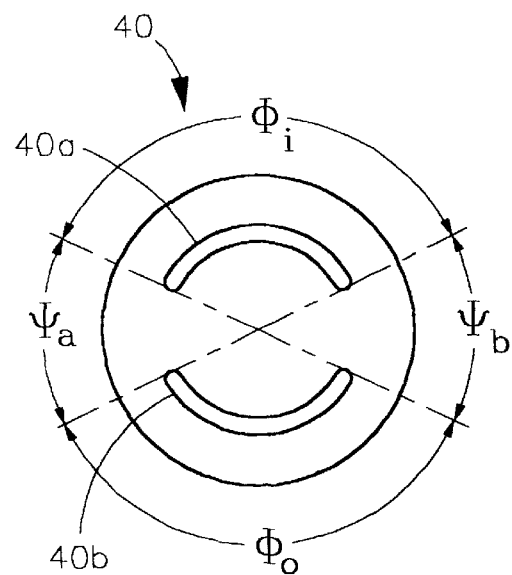

Critical parameters in the functioning of the pump 2 and pump head 8 include the number of pistons 12, the angles of the valve grooves 40a and 40b, the null-traverse angle, and piston diameter. For an understanding and analysis of these critical parameters, reference is now made to FIGS. 10A and 10B, in which are shown the angles alpha, theta, phi, and psi.

The angle alpha is defined as the angle subtended by the piston 12 diameter at the radial distance of the array of pistons 12.

The angle theta is defined as the angle subtended between pistons 12.

The angle phi is defined as the angle subtended by the inlet valve groove 40a and/or the outlet valve groove 40b. For the case of an asymmetrical arrangement of the grooves 40a and 40b, the angles are designated as $phi_o$ for the inlet groove 40a and $phi_i$ for the outlet groove 40b.

The angle psi is defined as the angle subtended by the "null-traverse" segments; i.e., the flat region between the ends of the inlet groove 40a and the outlet groove 40b. For the cases involving asymmetrical null-traverse segments, the angles are indicated by subscripts as $psi_a$ and $psi_b$.

n is defined as the number of pistons 12.

The following generalizations define optimum performance.

(1) For efficient sealing, 3 alpha is greater than or=psi.

(2) For symmetrical inlet and outlet grooves 40a and 40b, and null-traverse segments, phi+psi=180°, and $phi_i$=$phi_o$ (3) For asymmetrical inlet and outlet grooves 40a and 40b, and/or null segments, $phi_i$+$phi_o$+$psi_a$+$psi_b$=360°

(4) n theta=360°.

(5) The condition for reversible pulseless flow requires that $phi_i$ be greater than or=m theta, $phi_o$ be greater than or=m theta, where m is an integer between 1 and n−1.

(6) The machined slopes 30b and 30c of the cam groove 30a subtend angular displacements equal to $phi_i$ and to $phi_o$, and the flat areas 30d and 30e of the cam groove 30a subtend angular displacements equal to $psi_a$ and to $psi_b$, respectively.

It must be understood that for each port cap with a given angular arrangement of theta, phi, and psi, there is an accompanying cam cap/cam groove with a corresponding angular relationship—the flat zones of the cam groove corresponding to the "null traverse" segments of the port cap, and the rising/falling zones of the cam groove corresponding to the inlet/outlet valve grooves as required for a particular pump cycle.

From an analysis of the above parameters, the following conclusions are derived.

(1) A pump with a single piston will not provide pulseless flow.

(2) A pump or pump head utilizing two pistons will not provide bi-directional pulseless flow. However, the asymmetrical design illustrated in FIG. 5 should provide pulseless flow in one direction only.

(3) A pump configuration using three pistons has the least number of pistons that will yield pulseless flow in both directions. For three pistons the conditions for pulseless flow are:

$phi_i$=$phi_o$=120°, and $psi_a$=$psi_b$=60°.

(4) A design utilizing four pistons has at least two possible configurations providing bi-directional pulseless flow. A first configuration is represented by the equations $phi_i$=$phi_o$=90°, and $psi_a$=$psi_b$=90°

A second configuration is defined by the equations:

$phi_i$=90°, $phi_o$=180°, and $psi_a$=$psi_b$=45°

(5) Configurations with five pistons include one symmetrical arrangement and two asymmetrical arrangements of either valving grooves 40a, 40b or null-traverse segments.

From the above analysis, it will be apparent that (a) both odd and even numbers n of pistons 12 are capable of providing bi-directional pulseless flow, (b) the possible number of combinations of inlet/outlet groove 40a/40b angles $phi_i$/$phi_o$ increases significantly as the number n of pistons increases, and (c) both symmetrical and asymmetrical groove 40a, 40b designs are permissible. Still other configurations utilizing higher numbers n of pistons 12 will be apparent to those skilled in the art.

Reference is now made to

FIG. 5A, 5B, and 5C, which show how the valve grooves 40a, 40b, cam groove 30a, and rotating cylindrical body 31 cooperate to control flow for a two-piston pump 2. At the phase of the pump cycle shown in FIG. 5A, the piston 12 designated "A" is ending its compression stroke while "B" is beginning its compression stroke. At the phase of the pump cycle shown in FIG. 5C, "A" is starting its suction stroke, while "B" continues its compression stroke. At the phase of the pump cycle shown at right, "A" has completed its suction stroke, and is about to begin "null traverse" prior to beginning another compression stroke, while "B" is approaching the end of its compression stroke, and is about to enter "null traverse" prior to beginning its suction stroke. Note that during the compression stroke, the criterion for pulseless flow (i.e. one piston entering and one leaving the valve groove) are satisied. This criterion is NOT satisifed for the suction stroke, so that reversal of the direction of rotation would not satisfy the condition for bi-directional pulseless flow.

The pump 2 and pump head 8 are beneficially designed to include three or more pistons 12, to provide bi-directional pulseless flow. FIGS. 6A, 6B, and 6C shows three phases of a pump cycle for a three-piston configuration, the direction of rotation of the body 31 being graphically represented by an arrow. Note that for the three-piston case, the criterion for pulseless flow is satisfied for either direction of rotation.

Reference is now made to FIGS. 7A, 7B, and 7C, in which are shown three successive phases A, B, and C of a pump cycle for a four-piston pump 2. In FIG. 7A, phase A, pistons 12 "A" and "C" are traversing the "null" position, in which they are executing neither compression nor suction strokes. Piston 12 "D" is in the suction cycle, and piston 12 "B" in the compression cycle. In FIG. 7B, phase B, pistons 12 "A" and "C" are leaving null traverse and are about to begin compression and suction cycles, respectively. FIG. 7C, phase C, pistons 12 "B" and "D" are traversing the null position, piston 12 "A" is in the middle of its compression cycle, and piston 12 "C" is in the middle of its suction cycle. Note that once again, the condition for bi-directional pulseless flow is fulfilled by rotation in either direction.

Figure 8C:
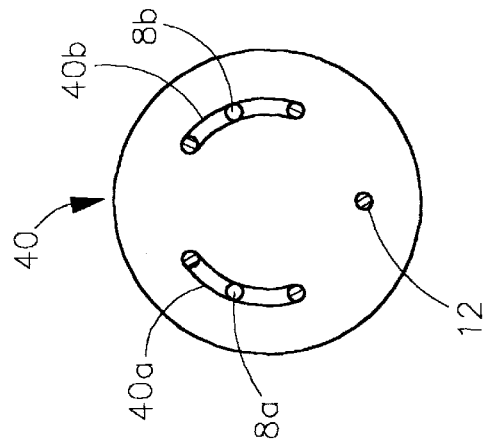
FIGS. 8A, 8B, and 8C are schematic representations of three port caps for three possible variations of a pump of the type shown in FIG. 1, each of which uses five pistons.
Figure 8B:
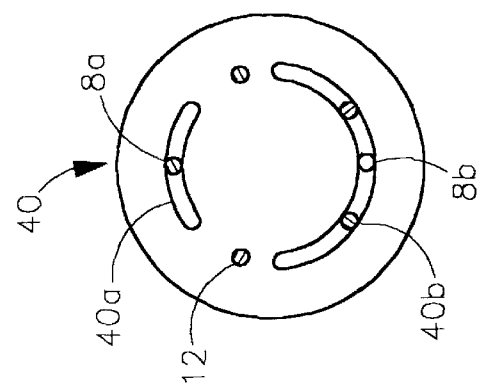
Figure 8A:
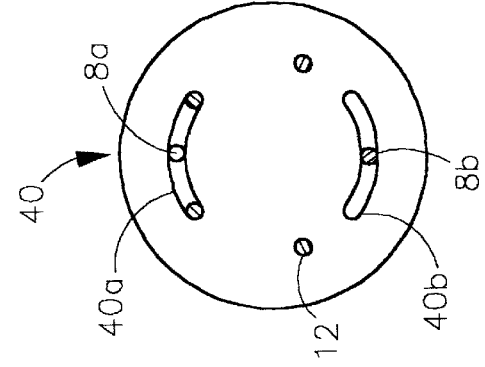

Reference is now made to FIGS. 8A, 8B, and 8C, in which are shown three possible configurations A, B, and C of a five-piston pump 2. Configurations obtainable with five pistons 12 include one symmetrical arrangement (A) and two asymmetrical arrangements (B and C) of either valving grooves 40a, 40b or null-traverse segments satisfying the criterion for bi-directional pulseless flow.

Figure 9D:
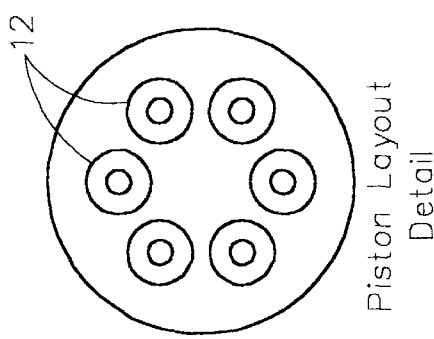
FIG. 9D is a schematic representation of the port cap shown in FIG. 9, showing the arrangement of the six pistons.

Reference is now made to FIGS. 9A, 9B, and 9C, in which are shown three successive phases, designated A, B, and C, of a pump cycle for a six-piston configuration. FIG. 9D, shows the piston 12 layout. FIGS. 9A, 9B, and 9C show end views of the port cap 40 with the positions of the six pistons 12, designated "A" through "F", superimposed thereon, and with the direction of rotation of the body 31 of the pump head 8 indicated by arrows. At A, pistons 12 "A" and "B" are moving clockwise toward the port cap 40, and thereby forcing fluid (not shown) toward the outlet port 8b; pistons 12 "C" and "F" are at the null position (not moving either forward or backward, but traversing across the surface of the port cap 40) and carrying their enclosed volumes of fluid from the inlet groove 40a to the outlet groove 40b, and pistons 12 "D" and "E" are moving away from the port cap 40, pulling fluid in from the inlet port 8a. At B, pistons 12 "C" and "F" are just moving off the null cycle, and are about to begin their compression and suction strokes, respectively; pistons 12 "B" and "E" are just moving onto the null cycle; and pistons "A" and "D" are in the middle of their compression and suction strokes, respectively. At C, pistons 12 "C" and "F" are in the null positions on opposite sides of the port cap 40, pistons 12 "A" and "B" are in the middle of their compression strokes, and pistons 12 "D" and "E" are in the middle of their suction strokes. At any time in the cycle, two pistons 12 are in compression, two in suction, and two at null.

Up to this point pump heads having only a single pumping channel have been considered. However, similar designs are possible which are capable of pumping multiple streams.

Figure 11A:
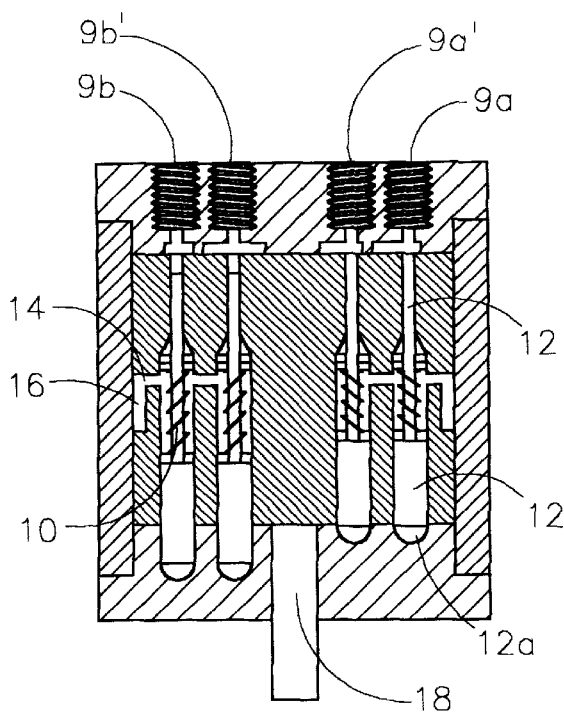
FIG. 11A is a vertical longitudinal cross-section of a pump head having dual inlet and outlet ports, and capable of pumping two streams, made in accordance with the principles of the present invention.
Figure 11B:
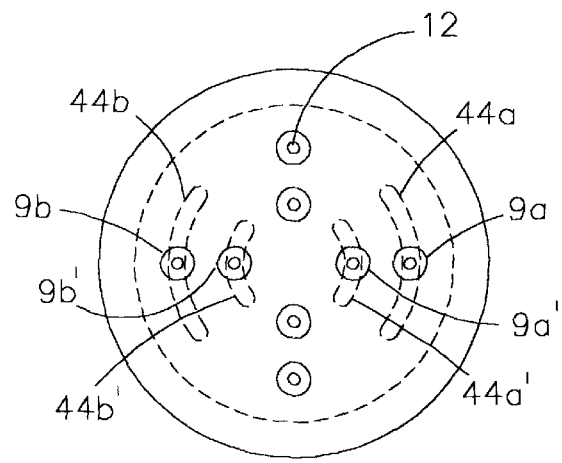
FIG. 11B is a schematic representation of cam and valve grooves for the pump head shown in FIG. 11A.

Reference is now made to FIG. 11A, in which is shown a cross-section of a pump head 9 of an eight-piston, two-stream configuration having two inlet ports 9a and 9a', two outlet ports 9b and 9b', and four pistons per channel. The arrangements of the pistons 12, cam and valve grooves for the pump head 9 is shown in FIG. 11B, to which reference is now made. A cam cap 32 is provided with a cam groove 32a; and a port cap 44 with inlet valve grooves 44a and 44b'. Of course, any number of pistons 12 per channel satisfying the conditions for pulseless, reversible flow are possible.

Figure 12A:
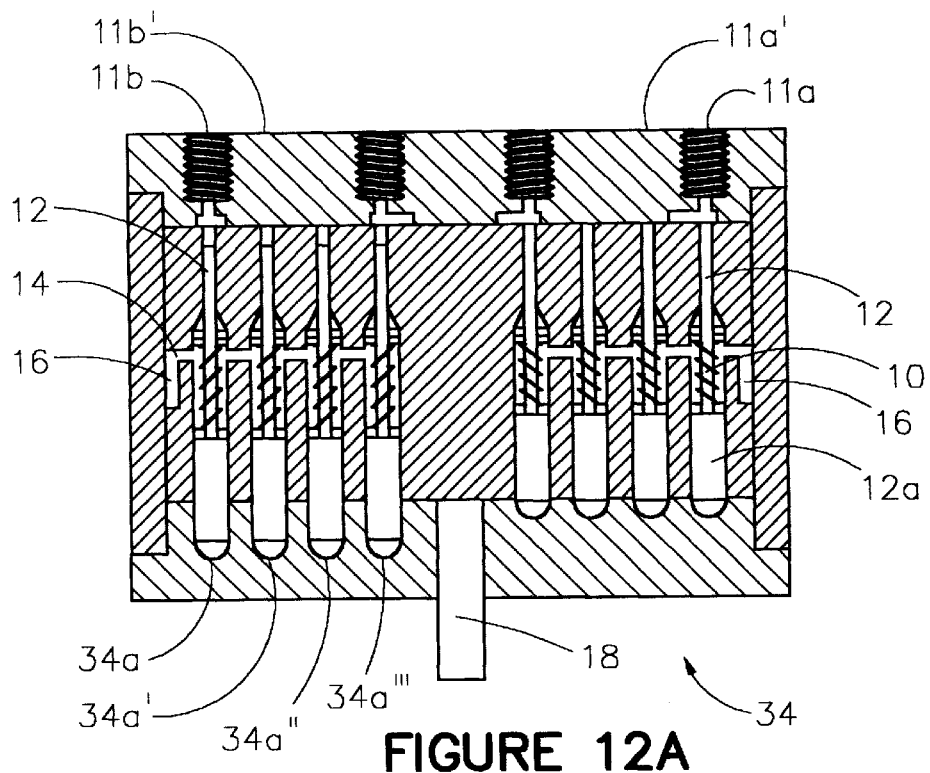
FIG. 12A is a vertical longitudinal cross-section of a pump head having four inlet and four outlet ports, and capable of pumping four streams, made in accordance with the principles of the present invention.

It is entirely feasible to extend the concept of multiple channels/streams to include a pump head of a sixteen-piston, four-stream configuration. A pump head 11 having four inlet (11a–11a''') and four outlet ports (11b–11b'''), only two each of which are shown, is schematically represented by FIG. 12A, to which reference is now made. The pump head 11 comprises two inlets ports 11a and 11a', which are shown, and two other inlet ports 11a'', and 11a''' (not shown) in a staggered configuration, to minimize the diameter of the pump. A cam cap 34 is provided with cam grooves 34a, 34a', 34a'', and 34a'''.

Figure 12B:
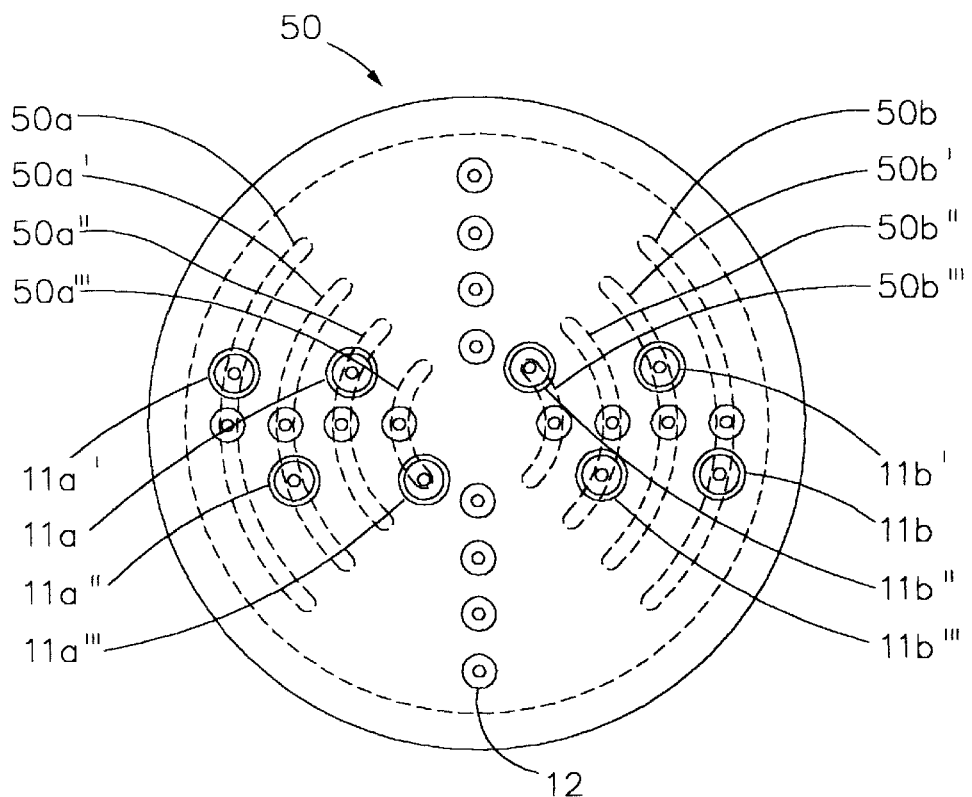
FIG. 12B is a schematic representation of cam and valve grooves for the pump head shown in FIG. 12A.

The arrangement of the associated cam and valve grooves, and of the sixteen pistons 12 for the pump head 11 is shown in FIG. 12B, to which reference is now made. A port cap 50 contains inlet grooves 50a, 50a', 50a'', and 50a''', and outlet grooves 50b, 50b', 50b'', and 50b''', inlet ports 11a 11a', 11a'', 11a''', and outlet ports 11b, 11b', 11b'', and 11b'''.

The multi-channel, multi-piston configurations of the pump heads 9 and 11, with minor modifications, yield a configuration whose arrangement provides a novel method of chemical analysis, which I shall call "pump-modulated simultaneous injection analysis" (PMSIA). This new method is similar to flow-injection analysis (FIA) in that it comprises the injection of constant-volume fluid segments into a flowing stream. However, unlike FIA, PMSIA further comprises the injection of constant-volume segments of a sample and of a reagent into one another, and thereafter the injection of an inert carrier fluid. PMSIA also differs from FIA in another respect: FIA utilizes a liquid-chromatograph style sample injection valve to inject the constant-volume segments, which makes a cycle of simultaneous injection very difficult to achieve. PMSIA, on the other hand, depends entirely on properties inherent in the configuration of the pump head, and therefore requires no injection valve. The pump itself provides complete control of the necessary injecting and cycling.

Figure 13:
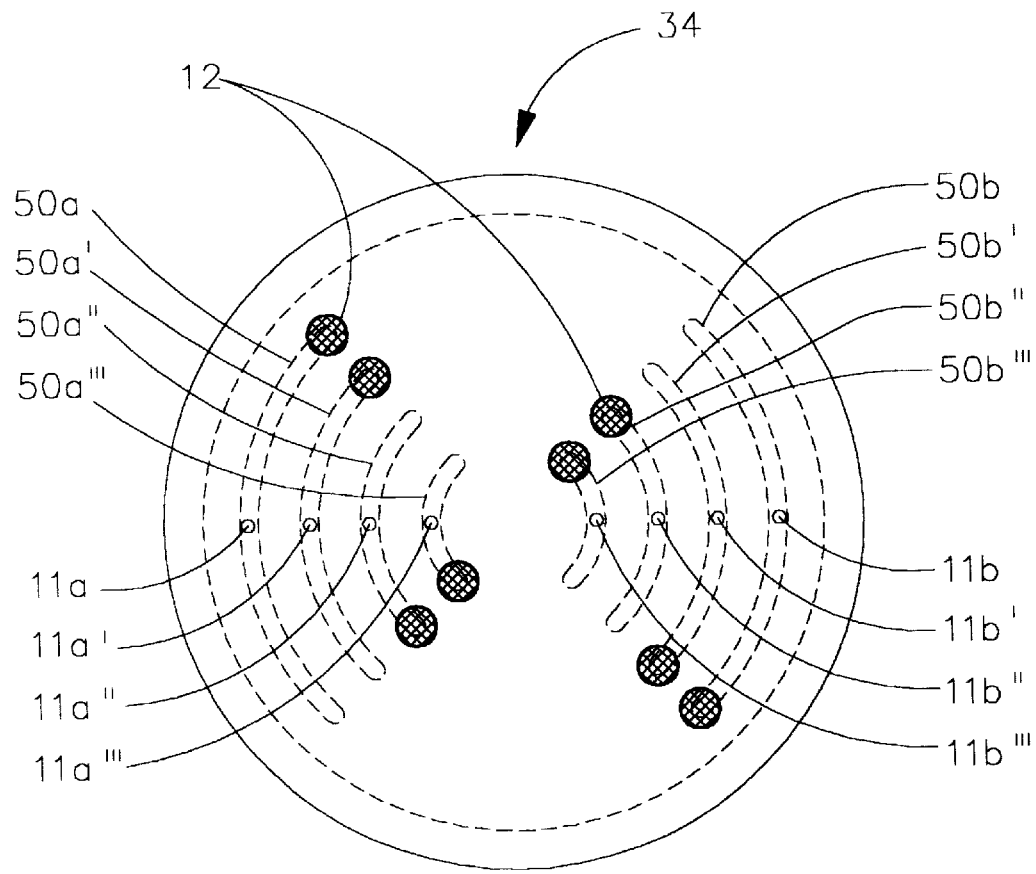
FIG. 13 is a schematic representation of a port cap showing the positions of eight pistons in a special-case usage of a multichannel embodiment enabling a new means for chemical analysis.

Referring now to FIG. 13, the positions of eight pistons 12 in the pump head 11, four inlet ports 11a, 11a', 11a'', and 11a''', and four outlet ports 11b, 11b', 11b'', and 11b''', are indicated schematically in FIG. 13, to which reference is now made. At the beginning of the pump cycle, the pistons 12 of valve grooves 50a'' and 50a''' are just reaching said inlet grooves, and the pistons 12 of valve grooves 50a and 50a' are just exiting said valve grooves. As the head 11 continues to rotate, the pistons 12 of grooves 50a'' and 50a''' traverse the inlet portion of their cycle, in which they aspirate a constant volume of fluid. As rotation continues, the pistons 12 of grooves 50a'' and 50a''' traverse the null position of their cycle, in which the pistons 12 hold a constant position in their respective cylinders 16, moving neither in nor out, but only rotating with the head 11. As rotation continues, the pistons 12 of inlet grooves 50a'' and 50a''' reach their respective outlet valve grooves 50b'' and 50b''', expelling their constant-volume segments through the outlet ports 11b'' and 11b'''. During this part of the rotation cycle, the pistons 12 of inlet grooves 50a and 50a' have been traversing the null portion of their cycle. As rotation continues, the pistons 12 of inlet grooves 50a and 50a' reach their respective outlet grooves 50b and 50b', expelling their segments of fluid through the outlet ports 11b and 11b'. This cycle is then repeated, with the opposing pistons 12 from each of the grooves 50a, 50a', 50a'', 50a''', 50b, 50b', 50b'', and 50b''' moving into and through their respective positions.

By using the grooves 11a, 11a', 11b and 11b' as valve grooves for a carrier fluid, grooves 11a'', and 11b'' as valve grooves for a fluid sample, and grooves 11a''' and 11b''' as valve grooves for a fluid reagent, there results an arrangement whereby the two aliquants (sample and reagent) are expelled together. By joining the flow paths of the two aliquants in channels outside the pump head (not shown), the aliquants are merged exactly "in phase". As rotation continues, the aliquants of carrier fluid are ejected with such timing as to immediately follow the sample and reagent aliquants, thus propelling the merged sample/reagent zone to analytical detection means.

The overall effect of a cycle utilizing the pump head 11 is to merge constant-volume portions of a sample stream with a reagent, and then drive the merged zone through mixing means and a detector with a larger volume of inert carrier fluid. The channels and grooves shown in FIG. 13 yield a configuration which completes two such cycles per single rotation of the pump rotor.

Reference is now made to FIGS. 14A, 14B, 14C, and 14D, in which are shown a second embodiment of a port cap for a pump made in accordance with the principles of the present invention and generally designated by the numeral 60. The pump is used with the port cap 60 for dispensing aliquants of a single stream into two different outlets 8b.

Reference is now made to FIGS. 15A, 15B, 15C, and 15D, in which are shown a third embodiment of a port cap for a pump made in accordance with the principles of the present invention, and generally designated by the numeral 62. The pump is used with the port cap 62 for merging and/or ratio/blending aliquants from two different streams. It should be noted that the port cap 62 is physically identical to port cap 60, only the inlet and outlet port functions are reversed.

Figure 16A:
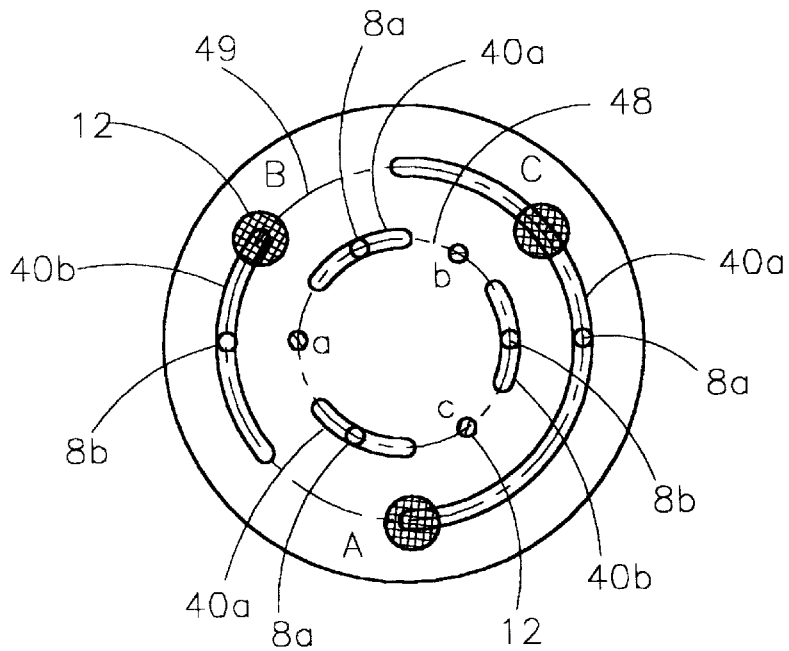

Reference is now made to FIGS. 16A, 16B, 16C, and 16D, in which are shown a fourth embodiment of a port cap for a pump made in accordance with the principles of the present invention, and generally designated by the numeral 64. Referring now to FIG. 16A, the fourth embodiment 64 uses a first pump channel 48 for merging and/or ratio/blending aliquants from two different streams (entering the port cap via inlet ports 8a, and leaving the port cap via outlet port 8b) and utilizing a second pump channel 49 to control a carrier fluid (entering the pump channel via inlet port 8a' propel, and leaving the port cap via outlet port 8b') to propel the merged and blended aliquants from pump channel 48 to analytical apparatus (not shown) through an external carrier channel (not shown). In FIG. 16A, blend/merge channel piston "c" has just begun its expulsion cycle, while "a" has just begun uptake of reagent, and "b" has just begun uptake of sample, while carrier channel piston "A" is just beginning "null traverse", and "B" and "C" are in their uptake stroke. In FIG. 16B, "a", "b", and "c" continue their respective strokes, "A" continues "null traverse", "B" begins null traverse, and "C" continues uptake. In FIG. 16C, "c" has completed its expulsion cycle, delivering a blended aliqant of reagent and sample to external channel (not shown), "b" has completed its uptake of reagent (and now contains mixed aliquants of sample and reagent), while "a" has just completed uptake of sample. "B" is just beginning its expulsion stroke, which will propel an aliquant of carrier immediately behind the aliquants previously delivered to the external channel by "a" through the external to analytical apparatus. "A" has begun uptake of carrier, and "C" contiues carrier uptake. As rotation continues, three analytical cycles will be delivered per single rotation of the pump rotor.

Reference is once again made to FIGS. 1 and 2, in which is shown a pump head 8 made in accordance with the principles of the present invention.

The pump head 8 has great modularity, allowing almost any stroke length, number of pistons 12, and piston diameter to be swapped out simply by an exchange of parts, permitting great freedom of choice in materials of construction of the individual components. It would only be necessary to construct the shaft 18, port cap 40, and pistons 12 of titanium, for instance; all other parts could remain 316 stainless steel. This could be accomplished by using titanium wire as a piston 12, silver-soldered into a hole drilled in the cylinder 16.

FIGS. 1 and 2 show a lubricant fill port 14 in the pump head 8. One of the advantages inherent in this particular pump design is the capability of filling all of the dead volume inside the cam cap 30, around the rotor shaft 18, and between the piston 12 seals (not shown) and the cylinders 16, with an inert lubricant. This feature imparts many significant advantages. First, filling all of this dead volume with a non-compressible liquid reduces the driving force for leakage of the pumped fluid into this space. Since the material is a lubricant, of course this assures maximum lubrication of all friction points. In particular, the action of the cylinders 16, as they move back and forth in the sleeves 33, facilitate this lubricant circulation. In particular, if the pump head 8 is oriented so that the maximum withdrawal of pistons 12 occurs as the bottom of the pump head 8, the lubricant will be forcefully circulated whether or not the entire dead volume is liquid-filled, as the space will fill with lubricant at the bottom of the rotation, and expel the lubricant at the top of the rotation.

The O-rings 35 shown in FIG. 1 serve to retain the lubricant within the pump head 8. The o-rings 35 serve no sealing function on the pumped fluid; this sealing is accomplished by the piston spring-loaded seals (not shown), and by the precise flat machining of the rotor shaft 18 port cap 40 mating surfaces. The inert lubricant will assist these mechanical seals as a secondary seal in conjunction with the rotary action. The immiscibility of the lubricant with most of the fluids being pumped should establish a thin inner cylinder of pumped liquid at the interface of the rotor shaft 18 and port cap 40, and a thin outer cylinder of lubricant. The boundary of these cylinders should be established at the outer diameter of the valve groove 40a machined into the port cap 40.

All of the advantageous features just detailed above should drastically extend the mean time between failure for this pump design.

While certain specific embodiments and details have been described in order to illustrate the present invention, it will be apparent to those skilled in the art that many modifications can be made therein without departing from the spirit and scope of the invention.

We claim:

1. A pump head for a piston-array pump, the pump head comprising:
   (a) a cylindrical casing having first and second ends,
   (b) a cylindrical body having first and second ends, rotatably disposed within the casing;
   (c) a cam cap at the first end of the cylindrical body, the cam cap incorporating a profile;
   (d) a port cap at the second end of the cylindrical body;
   (e) an inlet port;
   (f) an outlet port;
   (g) a plurality of at least three pistons, disposed within the cylindrical body, to provide capability of pulseless bidirectional fluid flow through the pump;
   (h) a cam follower for each piston; and
   (i) reciprocating means for each piston, the reciprocating means comprising the cam-cap profile;

the cam-cap, cam followers, and pistons being constructed and arranged so that at all times during which the cylindrical body is rotating at least one piston is in a compression mode; at least one piston is in a suction mode; and at least one piston is in a null mode, performing neither compression nor suction while traversing the surface of the port cap, thereby decoupling the rotational movement of the cylindrical body from the linear movement of the pistons to provide pulseless flow by the operation of the pump.

2. The pump head of claim 1, wherein the cam has on its interior surface a groove defining a geometric figure which:

(j) is circular;

(k) has a substantially semicircular cross-section;

(l) has a lowest surface, a highest surface, and a plurality of sloping surfaces connecting the lowest surface and the highest surface to one another; and (m) in combination with the cam followers controls the timing and depth of the strokes of the pistons.

3. The pump head of claim 1, wherein the port cap has on its interior surface:

(j) an inlet valve groove; and (k) an outlet valve groove;

the inlet and outlet valve grooves being constructed and arranged to provide the valving action which controls the direction of fluid flow.

4. The pump head of claim 2, wherein the port cap has on its interior surface:

(n) an inlet valve groove; and (o) an outlet valve groove;

the inlet and outlet valve grooves being constructed and arranged to provide the valving action which controls the direction of fluid flow.

5. The pump head of claim 4, wherein the number of pistons is three, and the conditions for pulseless flow are given by the equations:

(p) $phi_i = phi_o = 120°$; and (q) $psi_a = psi_b = 60°$;

where (r) $ph_i$=the angle subtended by the inlet valve groove 40a;

(s) $phi_o$=the angle subtended by the outlet valve groove 40b;

(t) $psi_a$=the angle subtended by the flat region between the ends of the inlet valve groove 40a and the outlet valve groove 40b; and (u) $psi_b$=the angle subtended by the flat region between the ends of the outlet valve groove 40b and the inlet valve groove 40a, as defined by FIG. 10.

6. The pump head of claim 4, wherein the number of pistons is four, and the conditions for pulseless flow are given by the equations:

(p) $phi_i = phi_o$; and (q) $psi_a = psi_b = 90°$;

where (r) $phi_i$=the angle subtended by the inlet valve groove 40a;

(s) $phi_o$=the angle subtended by the outlet valve groove 40b;

(t) $psi_a$=the angle subtended by the flat region between the ends of the inlet valve groove 40a and the outlet valve groove 40b; and (u) $psi_b$=the angle sub tended by the flat region between the ends of the outlet valve groove 40b and the inlet valve groove 40a;

as defined by FIG. 10.

7. The pump head of claim 6, wherein;

(p) the number of pistons is n;

(q) 3 alpha$>$/=psi;

(r) for symmetrical inlet and outlet grooves and null-traverse segments, $phi + phi_o = 180°$; and $phi_i = phi_o$;

(s) for asymmetrical inlet and outlet grooves and/or null-traverse segments, $phi_i + phi_o = 360°$; and (t) n theta=360°; where (u) $phi_i$=angle subtended by inlet valve groove 40a;

(v) $phi_o$=angle subtended by outlet valve groove 40b;

(w) $psi_a$=angle subtended by the flat region between the ends of the inlet valve groove 40a and the outlet valve groove 40b;

(x) $psi_b$=angle subtended by the flat region between the ends of the outlet valve groove 40b and the inlet valve groove 40a;

(y) alpha=angle subtended by the piston 12 diameter at the radial distance of the array of pistons 12;

(z) psi=angle subtended by the null-traverse segments=angle subtended by the flat region between the ends of the inlet valve groove 40a and the outlet valve groove 40b;

(a') phi=angle subtended by inlet valve groove 40a and/or outlet valve groove 40b;

(b') theta=angle subtended between pistons 12; and (c') m=an integer between 1 and n−1, as defined by FIG. 10.

8. The pump head of claim 7, wherein;

(y) $phi_i$$>$/=m theta; and (z) $phi_o$$>$m theta;

thereby providing pulseless flow from the pump head.

9. The pump head of claim 1, wherein the port cap has on its interior surface:

j) an inlet valve groove; and k) a plurality of outlet valve grooves;

the inlet and outlet valve grooves being constructed and arranged to provide the valving action which controls the direction of fluid flow, and to inject aliquants of a single stream into a plurality of different outlets.

10. The pump head of claim 2, wherein the port cap has on its interior surface:

n) an inlet valve groove; and o) a plurality of outlet valve grooves;

the inlet and outlet valve grooves being constructed and arranged to provide the valving action which controls the direction of fluid flow, and to inject aliquants of a single stream into a plurality of different outlets.

* * * * *